United States Patent
Nysaether et al.

(10) Patent No.: US 8,875,708 B2
(45) Date of Patent: Nov. 4, 2014

(54) VENTILATION DEVICE AND METHOD FOR CPR

(75) Inventors: Jon Nysaether, Hafrsfjord (NO); Kenneth George Morallee, Orpington (GB); Joar Eilevstjonn, Sandnes (NO)

(73) Assignee: Laerdal Medical AS, Stavanger (NO)

(*) Notice: Subject to any disclaimer, the term of this patent is extended or adjusted under 35 U.S.C. 154(b) by 1235 days.

(21) Appl. No.: 12/426,123

(22) Filed: Apr. 17, 2009

(65) Prior Publication Data

US 2009/0266364 A1 Oct. 29, 2009

(30) Foreign Application Priority Data

Apr. 18, 2008 (GB) .................................. 0807136.7

(51) Int. Cl.
| | |
|---|---|
| A62B 9/02 | (2006.01) |
| A62B 18/10 | (2006.01) |
| A61M 16/00 | (2006.01) |
| G09B 23/28 | (2006.01) |
| A61M 16/20 | (2006.01) |
| A61M 16/06 | (2006.01) |
| A61M 16/04 | (2006.01) |

(52) U.S. Cl.
CPC ....... *A61M 16/0048* (2013.01); *A61M 16/0084* (2014.02); *A61M 2205/581* (2013.01); *A61M 2205/583* (2013.01); *G09B 23/288* (2013.01); *A61M 16/201* (2014.02); *A61M 2016/0027* (2013.01); *A61M 16/06* (2013.01); *A61M 16/20* (2013.01); *A61M 16/04* (2013.01); *A61M 16/0078* (2013.01); *A61M 16/208* (2013.01); *A61M 2016/0021* (2013.01)
USPC ............ 128/205.24; 128/204.21; 128/204.23; 128/207.12

(58) Field of Classification Search
USPC ............ 128/204.18, 204.21, 204.23, 204.26, 128/205.13, 205.17, 205.24, 207.12
See application file for complete search history.

(56) References Cited

U.S. PATENT DOCUMENTS

| | | | |
|---|---|---|---|
| 4,163,450 A | 8/1979 | Kirk et al. .................. 128/145.8 |
| 4,622,964 A | 11/1986 | Flynn ....................... 128/205.24 |
| 5,005,568 A | 4/1991 | Loescher et al. .......... 128/202.28 |
| 5,730,122 A | 3/1998 | Lurie ........................ 128/207.12 |
| 6,155,257 A * | 12/2000 | Lurie et al. ............... 128/204.23 |
| 6,230,708 B1 | 5/2001 | Radko ...................... 128/205.24 |
| 6,526,973 B1 | 3/2003 | Lurie et al. ............... 128/205.24 |
| 2002/0170562 A1* | 11/2002 | Lurie et al. ............... 128/205.24 |
| 2003/0062040 A1 | 4/2003 | Lurie et al. ............... 128/203.11 |
| 2007/0056588 A1* | 3/2007 | Hayek ....................... 128/205.25 |
| 2008/0257344 A1* | 10/2008 | Lurie et al. ............... 128/203.11 |

OTHER PUBLICATIONS

Aufderheide, Tom P., et al., "Death by hyperventilation: A common and life-threatening problem during cardiopulmonary resuscitation", Crit. Care Med., vol. 32, No. 9, 2004 (Suppl.), pp. S345-S351.
Deakin, Charles D. et al., "Does compression-only cardiopulmonary resuscitation generate adequate passive ventilation during cardiac arrest?", Resuscitation 75, 2007, pp. 53-59.

* cited by examiner

*Primary Examiner* — Lynne Anderson
*Assistant Examiner* — Kathryn E Ditmer
(74) *Attorney, Agent, or Firm* — Dorsey & Whitney LLP

(57) ABSTRACT

Embodiments are directed to a ventilation device and method to be used on a patient during CPR. In one embodiment, the ventilation device comprises a housing having at least one opening for interfacing with a patient's airway, at least one valve configured to permit outflow of respiratory gases/air from the airway to ambient, a release mechanism for opening and closing an inlet passage to permit inflow of respiratory gases/air to the airway, and a control device for controlling the opening/closing of the inlet passage.

12 Claims, 4 Drawing Sheets

VENTILATION DEVICE AND METHOD FOR CPR

TECHNICAL FIELD

This invention is directed to ventilation devices, and more particularly one or more embodiments are directed to ventilation devices that may be used in combination with cardiopulmonary resuscitation.

BACKGROUND OF THE INVENTION

Cardiopulmonary resuscitation (CPR) is an emergency medial procedure for victims of cardiac arrest, respiratory arrest, or the like. Ventilation is an important part of CPR. In general, ventilation contributes to assisting or replacing spontaneous breathing. To provide ventilation often more than one person is needed. If only one medical professional is available, bystanders may be unwilling or unable to assist. Furthermore, when trained medical professionals are performing CPR, they often do not ventilate properly. Rather, they hyperventilate the patient or take too long to deliver ventilation.

During CPR, ventilation is usually carried out by forcing air into the lungs of the patient. This may be referred to as overpressure ventilation. During normal breathing, however, the volume of the chest cage is expanded by muscle activity and air is pulled into the lungs from ambient.

During CPR, if a bag-valve-mask or mouth-to-mouth technique is used, ventilation may not easily be performed while compressions are ongoing. Thus, it is typically recommended to stop compressions and ventilate twice for every 30 chest compressions. Often it takes a relatively long time to deliver these ventilations. As a result, the percentage of time with compression-induced blood flow is significantly reduced.

On the other hand, if a secure airway, such as an endotracheal tube is in place, a medical profession may be able to perform ventilations while compressions are ongoing. Therefore, no ventilation pauses are needed. However, these continuous ventilations are notoriously known to be performed at much too high of rates, creating a high percentage of time with overpressure in the lungs and in the thorax. This positive lung pressure is believed to inhibit venous blood return to the heart and thus limit the effect of chest compressions. This issue is, for example, discussed in: Aufderheide T P, Lurie K G: Death by Hyperventilation: *A common and life-threatening problem during cardiopulmonary resuscitation*. Crit Care Med 2004; 32 (9 Suppl): S345-S351.

A device for enhancing blood flow to the heart is described in U.S. Pat. No. 6,526,973. In particular, this patent describes an impedance threshold valve device employed for creating an under pressure inside the lungs that is believed to be beneficial for enhancing venous return to the heart. While being potentially beneficial for blood flow, a prolonged negative pressure inside the lungs may have other harmful effects to a patient. First of all, the underpressure may lead to pulmonary edema and/or atelectasis. Secondly, if overpressure ventilation is not carried out at regular intervals, the reservoir of oxygen in the lungs will soon be exhausted.

Typically, during chest compressions there is a certain gas exchange due to air being pushed out of the chest and pulled back in when the chest is released. However, it has been found that the exchanged volume is much less than the typical dead volume in the upper airways. Thus, the oxygen-rich air that enters the airway in the release phase of compressions seldom reaches the lungs, but is pushed out again during the next compression. Such passive, compression-driven "ventilation" is therefore not efficient for ventilating the lungs. This is described in further detail in: Deakin C D, O'Neill J F, Tabor T. "Does compression-only cardiopulmonary resuscitation generate adequate passive ventilation during cardiac arrest? Resuscitation." 2007 October; 75(1):53-9.

There is, therefore, a need for an improved device and method for providing pressure ventilation.

DETAILED DESCRIPTION

Embodiments of the present invention are directed toward ventilation devices, and more particularly one or more embodiments are directed to ventilation devices that may be used in combination with cardiopulmonary resuscitation. Certain details are set forth below to provide a sufficient understanding of the invention. However, it will be clear to one skilled in the art that the invention may be practiced without these particular details.

One or more embodiments are directed to a passive negative pressure ventilation device that may be used in conjunction with continuous chest compressions during CPR. In general, the ventilation device provides sufficient gas exchange to provide adequate oxygenation to the lungs. In one embodiment the ventilation device may comprise a housing having at least one opening for interfacing with a patient's airway, at least one valve arranged to permit an outflow of respiratory gases/air from the airway to ambient, a release mechanism that opens and closes a passageway to allow an inflow of respiratory gases/air to the airway, and a control device for controlling the device for opening and closing of the inflow passageway. In one embodiment, the gas is permitted to flow out through the valve to ambient while inflow of air is inhibited, such as by a one-way valve. In one embodiment, the release mechanism for opening and closing the inflow passageway is by a one-way inflow valve. The inflow valve may be repeatedly opened and closed to permit inflow of gas at particular time intervals.

Figure 1A:
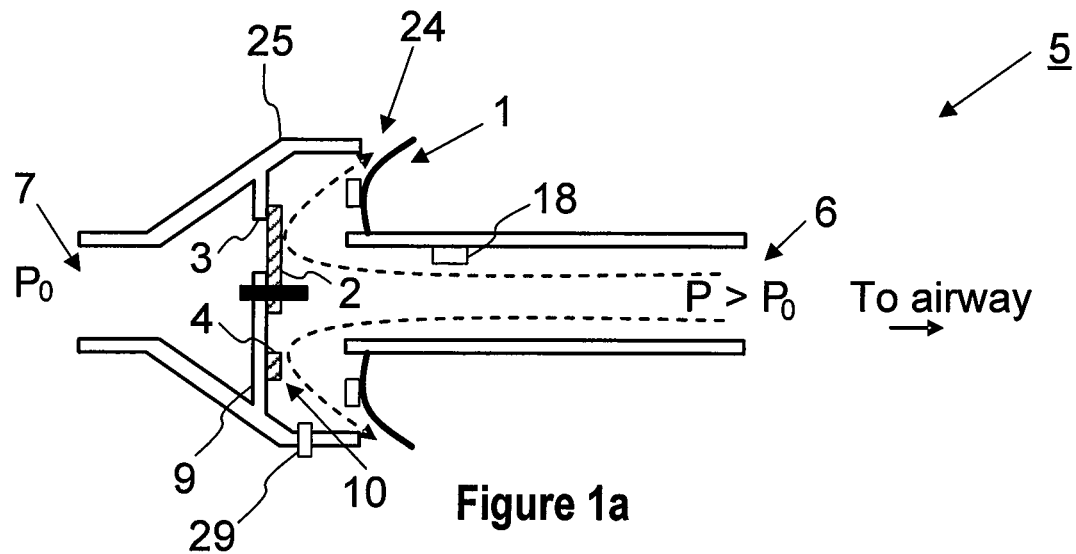
FIGS. 1*a*-1*c* are schematic illustrations of a cross sectional view of a ventilation device in three different states according to one embodiment of the invention.
Figure 1B:
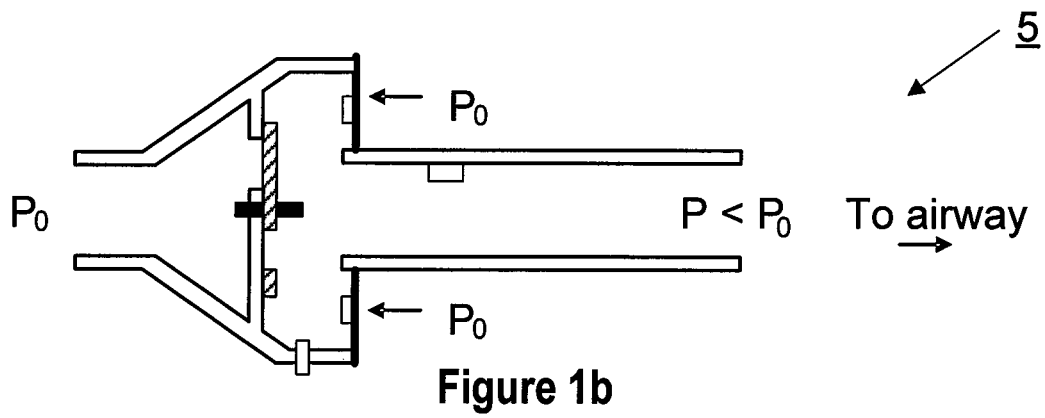
Figure 1C:
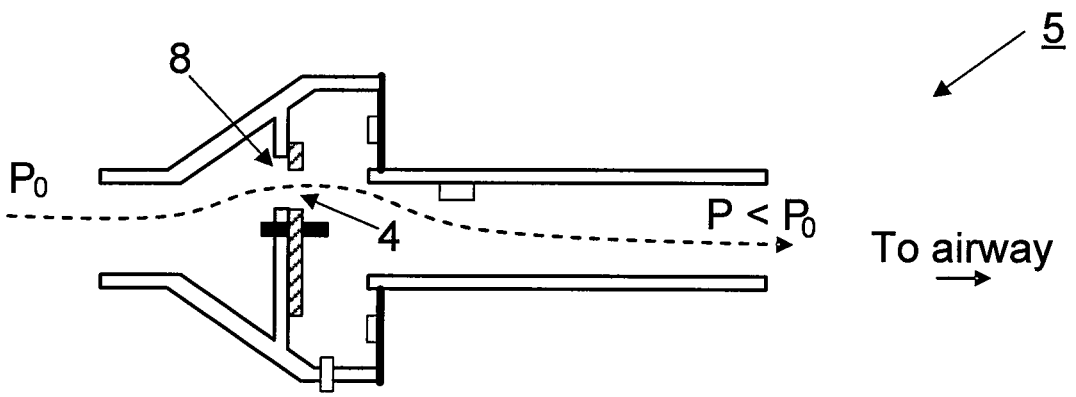

FIGS. 1*a*-1*c* are schematic illustrations of a cross section of a ventilation device 5 in three different phases of use according to one embodiment of the invention. In particular, FIG. 1*a* is schematic illustration of a cross-section of the ventilation device 5 when the chest of a patient is compressed. FIG. 1*b* is schematic illustration of a cross-section of the ventilation device 5 when the chest is released. FIG. 1*c* is schematic illustration of a cross-section of the ventilation device 5 during either chest compression and/or release.

As indicated above, the ventilation device 5 may be coupled to an airway of a patient. The ventilation device 5 may include a tube 6 operable to be inserted in or interface with the airway of the patient. In some embodiments, the tube 6 is coupled to a mask, an airway tube, or the like, that interfaces with or inserted in the airway of the patient. The ventilation device 5 further includes an opening 7 that may be coupled to ambient air. In another embodiment, the opening 7 is coupled to a gas source, such as oxygen.

The ventilation device 5 further comprises at least one valve 1 that allows air to flow from the lungs/airway of the victim to ambient through a respective outlet passage 24 in a frame 25. The valve 1 is configured so that air from ambient is inhibited or restricted from entering the device 5. In one embodiment, the valve 1 may be a rubber disk that rests on the frame 25, such as a plastic frame. The ventilation device 5 further includes a release mechanism 10. The release mechanism 10 includes a disk 2 that is mechanically coupled to a wall 9 so that the disk 2 may rotate relative to the wall 9. The wall 9 includes an opening 3 and the disk 2 includes an opening 4. The opening 3 in the wall 9 and the opening 4 in the disk 2 are positioned so that they are aligned or overlap each other during a part of a rotation of the disk 2. For instance, FIG. 1c shows the opening 3 in the wall 9 aligned with the opening 4 in the disk 2, thus creating an inlet passage 8 between the opening 7 and the tube 6 leading to the airway.

On the other hand, when the opening 3 in the wall 9 and the opening 4 in the disk 2 are positioned so that they do not overlap, the inlet passage 8 is blocked as in FIGS. 1a and 1b. During one revolution of the disk 2, the inlet passage 8 moves from "closed" to "open" and back to "closed." As will be clear to a person having ordinary skill in the art, the inlet passage 8 can be open and closed by other kinds of devices such as by a controllable one-way valve, a sliding plate, etc. Additionally, the disk 2 may include more openings so that one revolution of the disk 2 results in more openings of the inlet passage 8.

The use of the ventilation device 5 in conjunction with a CPR patient will now be described. In FIG. 1a the chest of the patient is compressed. The chest compression usually generates an overpressure in the lungs, forcing air out of the airway. At this stage the inlet passage 8 is closed. Air may escape to ambient through the one-way valve 1 causing air to flow out of the patient as is shown in FIG. 1a.

In FIG. 1b the chest of the patent is released. During this compression release, the chest will expand. Since there is now less air than before in the lungs and airway, there will be an underpressure inside the lungs. However, due to the one-way nature of the valve 1, air will not be able to re-enter because the inlet passage 8 is closed as is shown in FIG. 1b. Thus, the underpressure inside the lungs will be maintained. The next compression forces more air out of the lungs. Subsequent compressions continue to force air out of the lungs so that the amount of air in the lungs and the pressure in the lungs during release will continue to decrease for each compression as long as the inlet passage 8 is closed. Thus, with each chest compressions CO2-rich air will flow out of a victim's lungs to ambient through the one-way valve 1. Since air is not permitted to flow back in, an underpressure builds up inside the victim's chest.

FIG. 1c shows a cross-section of the ventilation device 5 during chest compression and/or release. The inlet passage 8 is open to ventilate the lungs and reduce the pressure difference between lungs/airway and ambient. In particular, the pressure difference between the lungs/airway and ambient will force fresh air to flow into the airway and thus ventilate the lungs. In one embodiment, the inlet passage 8 remains open long enough to permit air to flow back into the lungs so that the pressure difference in the airway/lungs relative to ambient is close to or at zero. In one embodiment, the inlet passage 8 may be sized such that the underpressure in the lungs is able to essentially equalize during the time the inlet passage 8 stays open.

In another embodiment, the inflow of gas is from an external gas source, such as an oxygen container or a pressurized air container. Once the gas has entered the lungs, the inlet passage 8 closes again and the cycle starts over. As compressions are provided to the chest of the patient, air flows out of the lungs/airway through the one way valve 1 and an underpressure again builds up inside the patient's lungs so that when the release mechanism 10 opens the inlet passage 8 again, fresh air will re-fills the lungs. Ventilation of the victim's lungs may be made without having to make pauses in compressions.

The release mechanism 10 may open the inlet passage 8 at particular time intervals, after a particular number of compressions, and/or in response to pressure spikes detected in the ventilation device. Additionally, the amount of time that the release mechanism 10 remains open may be based on a particular number of compressions, a particular amount of time, and/or until the pressure difference between the lungs and ambient has been reduced to a desired level, such as zero. In one embodiment the release mechanism 10 may be configured to open the inlet passage 8 at regular intervals, for instance every 6-20 seconds. Six seconds corresponds to a recommended frequency of 10 ventilations per minute, but a longer or shorter time may be used to assure efficient ventilation. During one interval, the inlet may for instance be open half the time and be closed half the time. Compressions to the chest may or may not be delivered while the inlet passage 8 is open.

In another embodiment, the release mechanism 10 may be configured to open the valve or inlet after a predetermined number of compressions, for instance 5-30. Typically, 10 compressions corresponds to 6 seconds at a recommended compression rate of 100/min, which again corresponds to the recommended frequency of 10 ventilations per minute. In one embodiment, the ventilation device 5 includes a mechanical or electrical counter that makes a count each time a pressure spike or outflow of air through the valve is detected. When the counter is full or reaches the predetermined number of compressions, for instance 5 compressions after the inlet was closed, a mechanical, electrical or combined mechanism opens the release mechanism 10 so that air is able to flow back into the airway and lungs. After a certain number of compressions, such as 5, or alternatively when the underpressure in the lungs is essentially zero, the release mechanism 10 is again closed for influx of air. In the above example, the release mechanism 10 stays open for 5 compressions, then closes for 5 compressions and then open again to maintain a ventilation frequency of approximately 10/minute at around 100 compressions/minute. In other embodiments, the absence of pressure spikes indicating compressions or outflow of air through the valve may be detected. This may be used to trigger a counter/timer that monitors/calculates the immediate and/or accumulated no compressions ("hands off") time. The current "hands off" time and requests to resume compressions again may be communicated to the rescuer through audible and/or visual means, such as a speaker, LEDs or a display integrated with the valve. Detection of extended hands off time may be used as a trigger to open the valve and keep it open until compressions are resumed. In yet another embodiment, the release mechanism 10 is adapted to open the valve when a certain underpressure in the lungs is reached, for instance 10 cm $H_2O$.

In reference to FIGS. 1a-1c, in one embodiment the opening 3 in the wall 9 and the opening 4 in the disk 2 are positioned so that each rotation of the disk 2 results in one sequence of the inlet passage 8 going from closed to open to closed again. Thus, one ventilation is delivered for each rotation of the disk 2. To assure ventilations at proper intervals, the disk 2 can be configured to rotate at particular speeds. For instance, in one embodiment, the disk 2 may be driven at a constant speed, such as ten times per minute.

In one embodiment, the ventilation device 5 comprises a pressure sensor for measuring the pressure of the patient's airway and/or lungs. In one embodiment, the measured pressure may be used to determine when to open the inlet passage 8. In particular, when the measured pressure has reached a particular level, the inlet passage 8 may be opened to permit the inflow of air in response to a signal from a control device. Similarly, the inlet passage 8 may be closed in response to a signal from the control device indicating a particular pressure has been reached. For instance, in the embodiment illustrated in FIG. 1, the pressure sensor 18 is provided in the tube 6. Each time a particular pressure is detected by the pressure sensor, the control device may send a signal indicating that the disk 2 is to be turned a particular angle. For instance, in one embodiment the disk 2 may be turned 36 degrees by a motor or a mechanical device. Therefore, ten chest compression may be performed per one revolution of the disk 2. As indicated above, if the patient's airways and lungs reach another level, the control device may send another signal indicating that the inlet passage 8 should be closed. In one embodiment, the pre-determined level used to close the inlet may be approximately equal to ambient pressure.

The pressure within the patient's airway and lungs may vary with time with increasing and decreasing underpressure as the inlet passage is alternately opened and closed. This results in local peaks in the pressure curve, called spikes, caused by external forces exerted on the lungs, such as, for example, chest compressions. Therefore, the rotation of the disk 2 may be controlled based on the pressure spikes generated by the chest compressions. Thus, by measuring the pressure in the airway and/or the lungs of the patient, the pressure or its derivatives may be used to control the opening and closing of the inlet passage 8.

Figure 2:
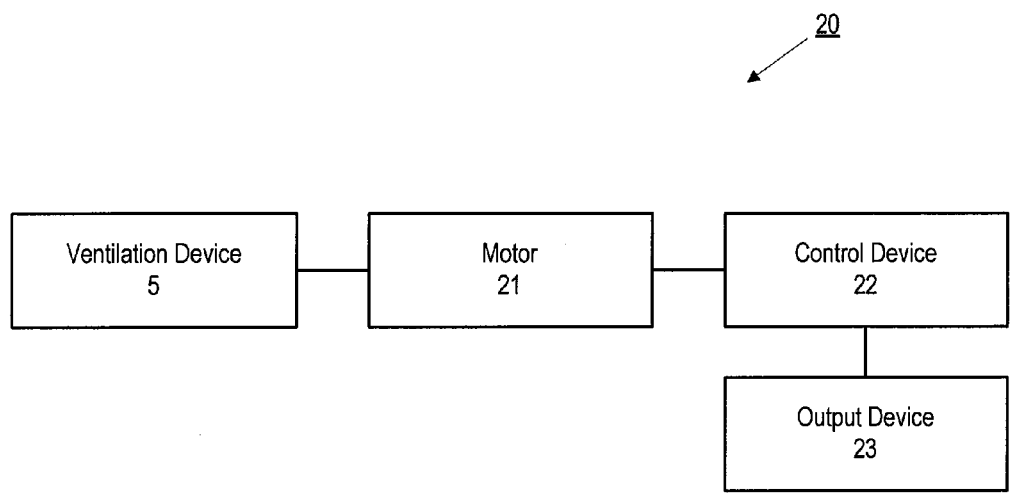
FIG. 2 is a block diagram of a system according to one embodiment of the invention.

The timing of the opening and/or closing of the inlet passage 8 can be controlled either by a mechanical device or by an electrically controlled device. In one embodiment, a control device, such as controller or microprocessor, may be coupled to the ventilation device 5. FIG. 2 is a block diagram illustrating a system 20 according to one embodiment of the invention. In particular, a control device 22 may be coupled to a motor 21 operable to cause the rotation of the disk 2 and thus control the opening and closing of the release mechanism 10 at particular time intervals depending on the type of valve used. Additionally, the control device 22 may be operable to control the valve 1 to control the outflow of gas through the outlet passage. The control device 22 may be further coupled to an output device 23 operable to communicate information to a user. For instance, the control device 22 may communicate information regarding the ventilation of the patient which may be relevant to the rescuer, such as pressure curve, time between pressure spikes, time without pressure spikes, etc. For instance, an inflow of air may be permitted in the inlet passage after a predetermined number of pressure spikes. In another embodiment and as will be explained further below, to eliminate the need for a battery, the rotation of the disk 2 may also be driven by a wind-up mechanism, such as those used in old clocks and watches.

The ventilation device 5 may be a stand alone unit operable to be coupled to an airway of a patient or it may be combined with another device that is connected to the airway of a patient. For instance, the ventilation device may be integrated with or adapted to be placed at the outer end of an oral airway, such as in combination with a nose clip, a laryngeal mask airway, a laryngeal tube, an endotracheal tube or other artificial airway.

In one embodiment, the ventilation device may be realized by modifying a standard resuscitation bag-valve-mask. A resuscitator bag-valve-mask may comprise a one-way outlet valve connected to the mask that prevents air from flowing back into the lungs. However, air is free to pass through an inlet valve between the bag and the mask, thus quickly equalizing out any underpressure in the lungs. Therefore, an occlusion may be added between the bag and the mask, such that the occlusion is configured to be opened and closed at certain intervals, thus enabling passive ventilation. In this embodiment, the bag may be removed. However, the bag may be used to provide additional overpressure ventilations or may be useful if for some reason there should be a pause in compressions.

In another embodiment, the ventilation device 5 is integrated in a face mask that can be pressed against the face of the victim, such as covering the nose and the mouth in such a way that the only pathway for air from the victim to ambient is through the one-way valve 1. In a cardiac arrest situation, with two rescuers, one rescuer may perform chest compressions on the patient while the other rescuer places the mask against the face of the victim, at the same time assuring open airways by tilting the patient's head backwards. In this embodiment, the mask can also be furnished with one or more elastic bands to be tightened around the head and neck of the victim, so that the mask can passively rest in place while a single rescuer performs chest compressions. The mask may also be integrated with an oral airway, laryngeal tube or similar to avoid airway occlusion by the tongue. The mask may be furnished with a bag in order to be able to perform overpressure ventilations if needed or connected to an oxygen supply with a slight overpressure to provide a more efficient delivery of oxygen to the lungs when the inlet passage 8 is open.

In another embodiment, the ventilation device 5 may be integrated with or used in combination with other resuscitation devices, such as a defibrillator or CPR quality monitoring device. As indicated above, a pressure sensor integrated near the valve may be used to measure the airway pressure, and the pressure spikes may be used to assess compression rate and efficiency. Opening and closing of the inlet passage 8 and the one way valve 1 may also be controlled by the resuscitation device according to resuscitation state and protocol.

The ventilation device according to one embodiment of the invention may comprise a leakage channel 29 in FIGS. 1a-1c permitting inflow of air if there is too great of an underpressure in the airway. The leakage channel 29 may be furnished with a controlled resistance or a valve with a threshold pressure between the airway and ambient. One purpose of such a leakage or valve is to assure that the pressure in the airway or lungs never drops below a certain value, even in the occasion where the mechanics that causes the inflow of air stops to work. The leakage may be coupled to a tube leading from ambient and as far down in the airway as possible, thus minimizing the dead volume between the leakage and the lungs. This will assure a more efficient exchange of air through the leakage.

As indicated above, in another embodiment the turning of the disk 2 may be entirely mechanical. In this embodiment, the turning of the disk 2 may be driven by the airway pressure spikes generated by the compressions. FIGS. 3a-3d are schematic illustrates of a top down view and a cross sectional view of a mechanically driven device in different states according to one embodiment of the invention. In this embodiment, the device comprises a wheel 11 with teeth and a hole 14, and a one-way valve 13 leading from the airway to ambient. In one embodiment, the number of teeth on the wheel is between 10 and 16. However, as will be clear to a person having ordinary skill in the art, the wheel may comprise any number of teeth.

The valve 13 may be coupled to an arm 12. A second one-way valve 15 leads from ambient to the airway. In some embodiments, the arm 12 is rotatably mounted so that it can move up and down and/or sidewise with respect to the valve 13. When the valve 13 is closed, the arm 12 is in a retracted position. When the valve 13 opens, such as is illustrated in FIG. 3, the arm will move forward to an extended position. The arm 12 may comprise a device for returning to its original position when the valve 13 closes in order to return the arm 12 to its retracted position. The purpose of the arm 12 is to rotate the wheel 11 by one step corresponding to one tooth for each compression.

Figure 3A:
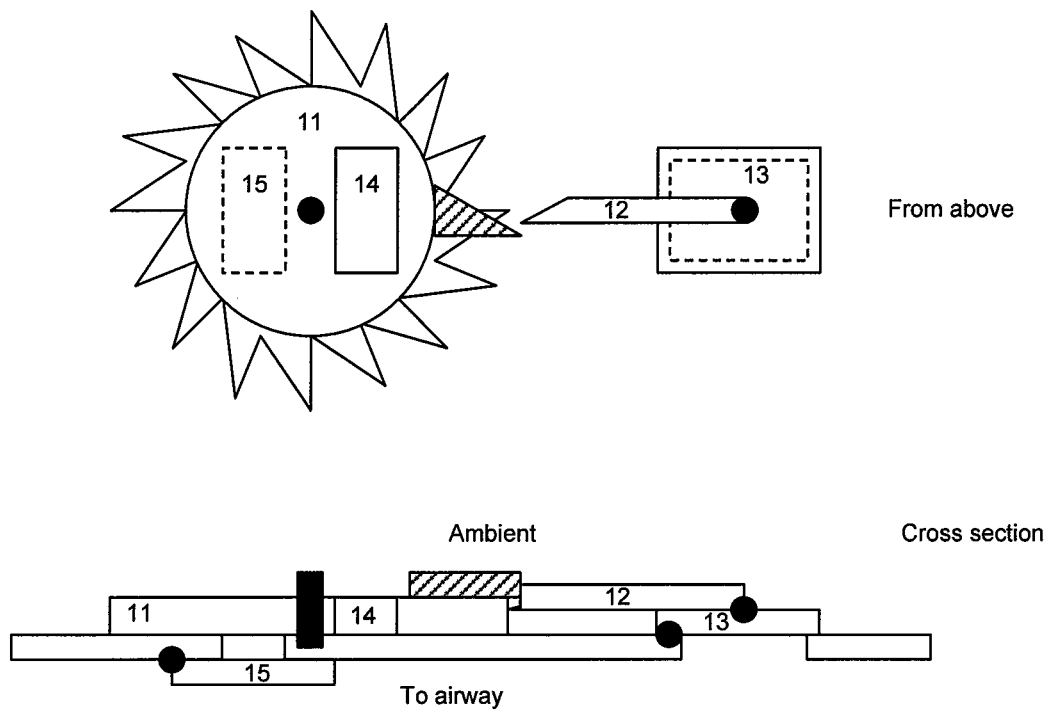
FIGS. 3*a*-3*d* are schematic illustrates of a top down view and a cross sectional view of a mechanically driven device in different states according to one embodiment of the invention.
Figure 3B:
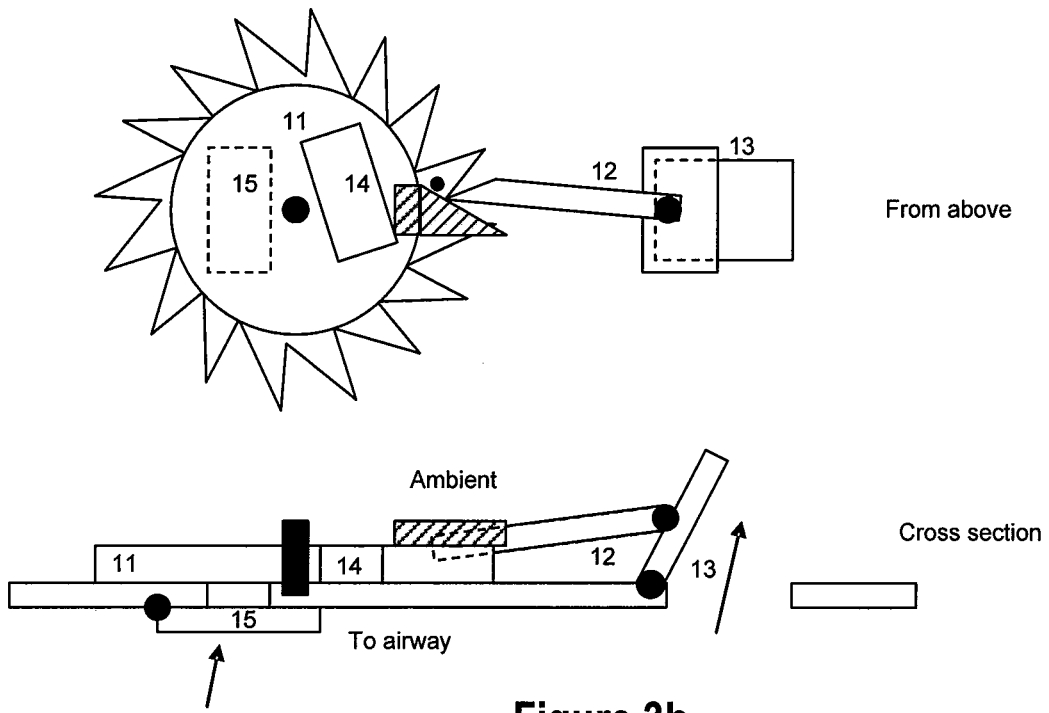

FIG. 3a illustrates the device before chest compressions have started. The one-way valves 15 and 13 are both closed and the arm 12 is in a retracted position not contacting the wheel 11. FIG. 3b illustrates the device during a chest compression. In the compression phase, there is an overpressure generated in the airway system. This overpressure causes the one-way valve 13 to open, so that air can escape, at the same time causing the arm 12 to move forward and in contact with a tooth of the wheel 11 and a guide means 16. The further forward movement of the arm 12 will push on the arm 12 so that the wheel rotates one step. In the compression release phase, the overpressure will disappear, the one-way valve 13 again closes and the arm 12 is retracted to its original position as illustrated in FIG. 3a, but with the hole 14 of the wheel 11 shifted in the rotational direction. Because air has been pushed out of the airway, there is now an underpressure in the airway relative to ambient. However, the wheel 11 prevents air from flowing back through the one-way valve 15, so that the pressure in the airway is not able to equalize with the ambient. For each compression, the same procedure is repeated, with the result that the wheel 11, and thus the hole 14, rotates one step for each compression, and that the underpressure in the airway gradually increases.

Figure 3C:
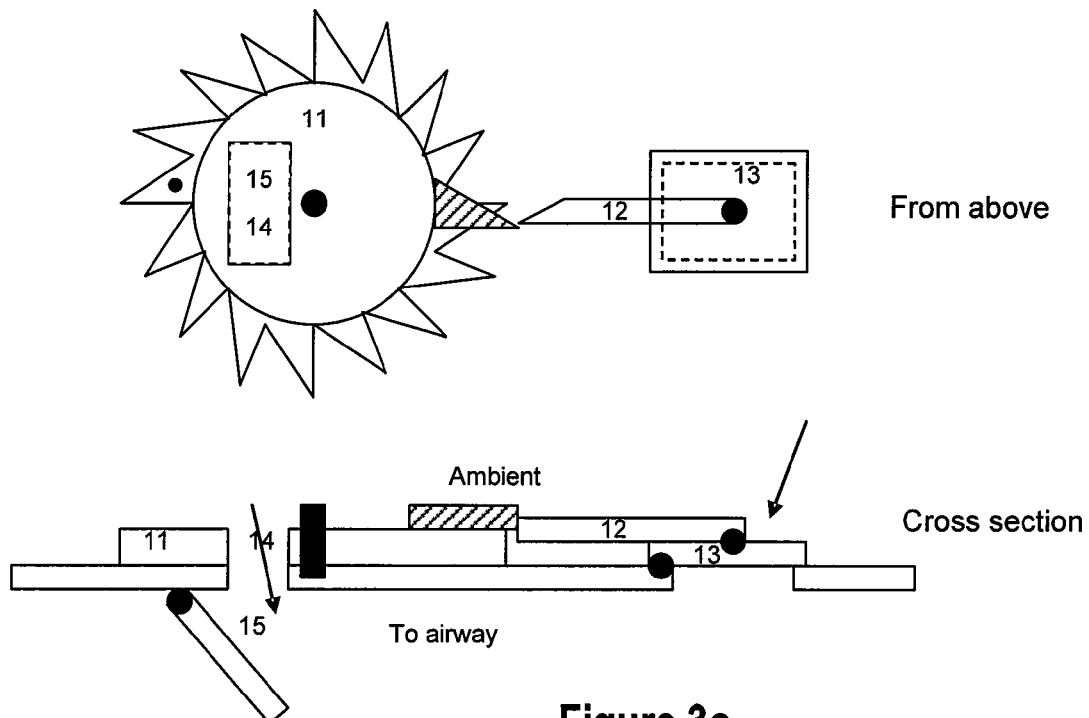

After a number of compressions, such as 4-6 from its original position in FIG. 3a, the wheel 11 has rotated so far that there is an overlap between the hole 14 in the wheel 11 and the one-way valve 15. This state is illustrated in FIG. 3c. During compression release in this situation, since there is an underpressure in the airway, air will now flow back into the airway from ambient through the one-way valve 15, thus ventilating the patient with fresh air. The one-way valve 13 is closed during release of the chest compression.

Figure 3D:
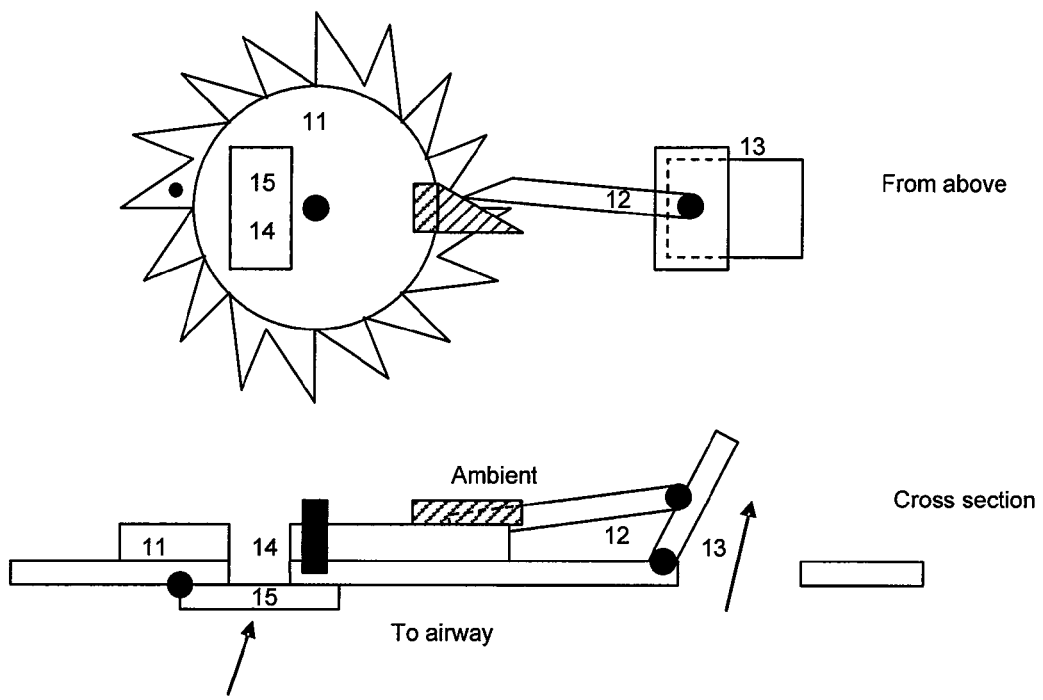

When the opening 14 in the wheel 11 and the one-way valve 15 are aligned, chest compressions will still create an overpressure in the airway. FIG. 3d illustrates the one-way valve 15 closed and the one-way valve 13 opened. This will in turn move the arm 12 forward, which causes the wheel 11 to rotate one step. Thus, wheel rotation continues until a full turn has been made, whereby full ventilation has been supplied to the patient. A new turn then starts. Thus, one ventilation is given for each 16 compressions for as long as the chest is under compression.

Although the present invention has been described with reference to the disclosed embodiments, persons skilled in the art will recognize that changes may be made in form and detail without departing from the spirit and scope of the invention. Such modifications are well within the skill of those ordinarily skilled in the art. Accordingly, the invention is not limited except as by the appended claims.

The invention claimed is:

1. A ventilation device, comprising:
 a housing having at least one outlet passage for allowing, gas to be expired from the. lungs of a patient and at least one inlet passage for allowing gas to be provided the lungs of the patient;
 at least one valve provided at the outlet passage configured to allow gas to flow out of the housing to ambient while inhibiting gas from entering through the outlet passage;
 at least one release mechanism provided at the inlet passage and configured to periodically open and close the inlet passage during chest compressions to control inflow of gas through the inlet passage, the at least one release mechanism further configured to close the inlet passage when pressure in the lungs of the patient equals ambient pressure; and
 a control device operable to control the opening and closing of the at least one release mechanism, wherein the at least one release mechanism includes a disk rotatably coupled to the housing, the disk having a disk opening and the control device is configured to rotate the disk relative to the housing each time a chest compression is detected to periodically align the disk opening with an opening of the housing to open the inlet passage.

2. The ventilation device according to claim 1 wherein the gas that flows into the housing, is provided by ambient air or by an external gas source.

3. The ventilation device according to claim 1 further comprising a pressure sensor operable to measure the pressure in the housing.

4. The ventilation device according to claim 1 wherein the release mechanism is an inflow valve.

5. The ventilation device according to claim 3 wherein the control device is further configured to detect pressure spikes and open the release mechanism after a predetermined number of pressure spikes have been detected.

6. The ventilation device according to claim 3 further comprising a leakage channel that permits an inflow of gas into an airway of the patient if an underpressure in the airway is detected.

7. The ventilation device according to claim 3 further comprising an output device operable to communicate at least one of a pressure, a pressure curve, time between pressure spikes, number of chest compressions, or an indication to change the position of the release mechanism.

8. The ventilation device according to claim 1 wherein the periodic alignment intervals range from 6 seconds to 20 seconds.

9. The ventilation device according to claim 1 wherein the at least one release mechanism is configured to remain closed for a particular number of chest compressions.

10. The ventilation device according to claim 9 wherein the particular number of chest compressions range from 5 chest compressions to 30 chest compressions.

11. The ventilation device according to claim 1 further comprising a counter configured to measure a number of chest compressions.

12. A ventilation device, comprising:
 a housing having an outlet passage for allowing a gas to be expired from the lungs of a patient and an inlet passage for providing gas to the kings of the patient;
 at least one valve provided at the outlet passage, the valve configured to allow gas to flow out of the outlet passage to ambient while inhibiting gas from entering through the outlet passage;
 at least one release mechanism provided at the inlet passage configured to open and close the inlet passage to control inflow of gas through the inlet passage during chest compressions;
 a control device operable to control the opening and closing of the at least one release mechanism, the at least one release mechanism including a disk rotatably coupled to the housing, the disk having a disk opening and the control device is configured to rotate the disk relative to the housing each time a chest compression is detected to periodically align the disk opening with an opening of the housing to open the inlet passage; and wherein the at least one release mechanism is configured to open the inlet passage to allow gas to flow into the housing at particular time intervals.

* * * * *